US010975194B2

(12) United States Patent
Watanabe

(10) Patent No.: US 10,975,194 B2
(45) Date of Patent: Apr. 13, 2021

(54) POLYCARBONATE RESIN, AND POLYCARBONATE RESIN COMPOSITION

(71) Applicant: IDEMITSU KOSAN CO., LTD, Tokyo (JP)

(72) Inventor: Nobuhiro Watanabe, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 16/376,197

(22) Filed: Apr. 5, 2019

(65) Prior Publication Data
US 2019/0233584 A1 Aug. 1, 2019

Related U.S. Application Data

(63) Continuation of application No. 15/121,314, filed as application No. PCT/JP2015/055091 on Feb. 23, 2015, now abandoned.

(30) Foreign Application Priority Data

Feb. 28, 2014 (JP) .................. 2014-039521

(51) Int. Cl.
| | | |
|---|---|---|
| C08G 64/06 | (2006.01) |
| C08K 5/524 | (2006.01) |
| C08L 69/00 | (2006.01) |
| C08L 83/04 | (2006.01) |
| C08L 83/06 | (2006.01) |
| C08L 83/08 | (2006.01) |
| C08K 5/00 | (2006.01) |
| B29D 11/00 | (2006.01) |
| C07C 39/16 | (2006.01) |
| C08G 77/14 | (2006.01) |
| C08G 77/20 | (2006.01) |
| C08G 77/26 | (2006.01) |
| C08G 77/28 | (2006.01) |
| C08G 77/18 | (2006.01) |

(52) U.S. Cl.
CPC ........ C08G 64/06 (2013.01); B29D 11/00663 (2013.01); C07C 39/16 (2013.01); C08K 5/005 (2013.01); C08K 5/524 (2013.01); C08L 69/00 (2013.01); C08L 83/04 (2013.01); C08L 83/06 (2013.01); C08L 83/08 (2013.01); C08G 77/14 (2013.01); C08G 77/18 (2013.01); C08G 77/20 (2013.01); C08G 77/26 (2013.01); C08G 77/28 (2013.01)

(58) Field of Classification Search
CPC .......... C08L 83/08; C08L 83/06; C08L 83/04; C08L 69/00; C08K 5/524; C08K 5/005; C08G 64/06; C07C 39/16
USPC ......................................................... 524/120
See application file for complete search history.

(56) References Cited

U.S. PATENT DOCUMENTS

| | | | | |
|---|---|---|---|---|
| 4,880,896 A * | 11/1989 | Otsubo | .................. | C08G 64/40 528/196 |
| 5,438,086 A * | 8/1995 | Stevenson | .............. | C08K 5/527 524/120 |
| 5,648,561 A * | 7/1997 | Tan | .......................... | C07C 37/20 568/724 |
| 5,696,295 A | 12/1997 | Wulff et al. | | |
| 6,689,464 B1 | 2/2004 | Lanze et al. | | |
| 2002/0137827 A1 | 9/2002 | Tomioka et al. | | |
| 2003/0007764 A1* | 1/2003 | Hirota | ...................... | C08K 3/22 385/129 |
| 2003/0055200 A1 | 3/2003 | Ando et al. | | |
| 2004/0142139 A1 | 7/2004 | Tomioka et al. | | |
| 2004/0143048 A1 | 7/2004 | Tomioka et al. | | |
| 2004/0147713 A1 | 7/2004 | Tomioka et al. | | |
| 2007/0213452 A1 | 9/2007 | Kawato et al. | | |
| 2008/0144324 A1* | 6/2008 | Tahara | .................. | B29C 45/561 362/311.06 |
| 2012/0309874 A1* | 12/2012 | Takimoto | ................ | C08G 65/20 524/120 |
| 2014/0364546 A1 | 12/2014 | Okamoto et al. | | |

FOREIGN PATENT DOCUMENTS

| | | |
|---|---|---|
| CN | 1080914 A | 1/1994 |
| CN | 1112103 A | 11/1995 |
| CN | 1118155 A | 3/1996 |
| CN | 1366542 A | 8/2002 |
| CN | 1395693 A | 2/2003 |
| CN | 1466605 A | 1/2004 |
| CN | 1918097 A | 2/2007 |
| CN | 1942521 A | 4/2007 |
| CN | 101142444 A | 3/2008 |
| CN | 102449067 A | 5/2012 |
| CN | 102686671 A | 9/2012 |
| DE | 44 13 396 A1 | 10/1995 |
| EP | 0 293 769 A2 | 12/1988 |
| EP | 0 683 761 A1 | 11/1995 |
| EP | 1 331 235 A1 | 7/2003 |
| JP | H07-285902 A | 10/1995 |
| JP | H08-509466 A | 10/1996 |
| JP | 2001-344813 A | 12/2001 |
| JP | 2002-173530 A | 6/2002 |
| JP | 2005-075736 A | 3/2005 |
| JP | 2006-335850 A | 12/2006 |
| JP | 2010-275484 A | 12/2010 |
| JP | 4621312 B2 | 1/2011 |

(Continued)

OTHER PUBLICATIONS

International Search Report issued in International Patent Application No. PCT/JP2015/055091 dated May 19, 2015.

(Continued)

Primary Examiner — Doris L Lee
(74) Attorney, Agent, or Firm — Foley & Lardner LLP

(57) ABSTRACT

Provided is a polycarbonate resin, including, as a raw material, a bisphenol A having 100 ppm by mass or less of isopropenylphenol and 250 ppm by mass or less of 2-(2-hydroxyphenyl)-2-(4-hydroxyphenyl)propane, each detected after heating in air at 175° C. for 1 hour.

20 Claims, No Drawings

(56) References Cited

FOREIGN PATENT DOCUMENTS

| JP | 2011-174031 A | 9/2011 |
| JP | 2013-139097 A | 7/2013 |
| JP | 2013-227510 A | 11/2013 |
| KR | 10-0375082 B1 | 5/2003 |
| WO | WO-94/19302 A1 | 9/1994 |
| WO | WO-2010/137611 A | 12/2010 |
| WO | WO-2013/100090 A1 | 7/2013 |

OTHER PUBLICATIONS

Office Action dated Jul. 5, 2017 in Chinese Patent Application No. 201580010507.8.
Chinese Office Action dated Apr. 28, 2018 in corresponding Application No. 201580010507.
Propylene Derivative Engineering, Book by Zhang, Xuzhi et al., ISBN 7-5025-1500-3, Publication No. 039, May 1995.
European Office Action dated Jun. 21, 2018 in corresponding Application No. 15755516.0.
Japanese Office Action dated Sep. 4, 2018 in corresponding Application No. 2016-505209.
Taiwanese Office Action dated Nov. 25, 2019 for corresponding Application No. 108111450.
Office Action dated Mar. 3, 2020 for corresponding Japanese Application No. 2019-096770.
Office Action dated Feb. 11, 2020 for corresponding Saudi Arabian Patent Application No. 516371732.
Office action dated Jun. 23, 2020 for corresponding Taiwanese Patent Application No. 108111450.
Office Action dated Dec. 3, 2020 for corresponding South Korean Patent Application No. 10-2016-7023250
"Chemical Industry Production Flow Diagram (Part II)", Chemical Industry Press Co., Ltd., Jan. 30, 1996, p. 387.
Office Action dated Dec. 1, 2020 for corresponding Chinese Patent Application No. 201910094550.7.

* cited by examiner

POLYCARBONATE RESIN, AND POLYCARBONATE RESIN COMPOSITION

CROSS-REFERENCE TO RELATED PATENT APPLICATIONS

This application is a continuation of U.S. patent application Ser. No. 15/121,314, filed on Aug. 24, 2016, which is a National Stage of International Patent Application No. PCT/JP2015/055091, filed Feb. 23, 2015, which is based upon and claims the benefit of priority of Japanese Patent Application No. 2014-039521, filed on Feb. 28, 2014. The contents of these applications are incorporated herein by reference in their entireties.

TECHNICAL FIELD

The present invention relates to a polycarbonate resin and a polycarbonate resin composition, which are available by selecting and using a specific raw material, and have a satisfactory hue. More specifically, the present invention relates to a polycarbonate resin and a polycarbonate resin composition each having a reduced yellow tint (low YI value) and an excellent light transmission property.

BACKGROUND ART

A polycarbonate resin (hereinafter sometimes abbreviated as "PC resin") is excellent in, for example, transparency, mechanical characteristics, thermal stability, electrical properties, and weatherability, and hence has been used in an optical molded article, such as a light-guiding plate, a lens, or an optical disc, by taking advantage of such characteristics. However, the light transmission property of the resin is lower than that of a polymethyl methacrylate (PMMA) or the like, and hence its color tone has a slightly yellow tint.

Particularly in the case where the light-guiding length of a light-guiding plate using the resin becomes longer, when the material has a yellow tint, a light beam having a shorter wavelength is absorbed. Accordingly, there occurs a phenomenon in which a difference in color tone between a portion close to a light source and a portion distant therefrom is observed, and there occurs a problem in that the color tone becomes nonuniform. A polycarbonate material having a reduced yellow tint has been required for solving such problem.

With regard to a light-guiding plate or the like, the thinning and upsizing of such product have been progressing. Therefore, there has been a growing requirement for a molding material having high flowability and suppressed in yellowing even in injection molding at high temperature.

A thin-walled product obtained by injection molding at high temperature has heretofore been typically applied to, for example, a digital versatile disc (DVD). In the application, however, required quality in terms of a color tone is not as high as that in a light-guiding member because a required light transmission length is as short as the thickness direction of the disc (about 0.6 mm).

In Patent Document 1, there is a disclosure of a method involving setting the total amount of specific eight kinds of impurities in a polycarbonate resin to 750 ppm by mass or less to reduce the number of white spots in an optical disc substrate and an error rate therein.

In Patent Document 2, there is a disclosure of a polycarbonate resin composition for an optical disc substrate containing a polycarbonate resin produced by using, as a raw material, 2,2-(4-hydroxyphenyl)propane (bisphenol A) in which the content of a cyclic dimer of p-isopropenylphenol is 150 ppm by mass or less and the content of trisphenol is 150 ppm by mass or less, and 100 ppm by mass to 500 ppm by mass of a release agent, the resin composition having a feature in that the viscosity-average molecular weight of the resin composition in a pelletized state is from 10,000 to 17,000, and the hydroxyl group terminal content thereof is less than 7 mol %. The amount of 2-(2-hydroxyphenyl)-2-(4-hydroxyphenyl) propane (2,4-isomer) in the polycarbonate resin composition is 1,000 ppm by mass or less.

In Patent Document 3, there is a disclosure of a method of producing an aromatic PC including the step of retaining the molten state of the composition of bisphenol A and phenol, which is obtained in an apparatus for producing bisphenol A, under high temperature with an inert gas (nitrogen gas) without granulating the composition, followed by the supply of the composition to a subsequent PC production apparatus. In Patent Document 3, there is a disclosure that the content of 4-isopropenylphenol in the composition of 2,2-(4-hydroxyphenyl)propane and phenol retained in a molten state to be subjected to the polymerization of the polycarbonate is 1,000 ppm by mass or less.

CITATION LIST

Patent Document

[Patent Document 1] JP 4621312 B2
[Patent Document 2] JP 2001-344813 A
[Patent Document 3] JP 2002-173530 A

SUMMARY OF THE INVENTION

Technical Problem

As disclosed in Patent Documents 1 to 3, various attempts have been made to obtain a polycarbonate resin having a reduced amount of impurities through, for example, the improvement of a production method for a polycarbonate resin. However, it is difficult to achieve a low level of YI value even by those methods. The present invention has been made to solve such problems, and an object of the present invention is to achieve a low YI value not by paying attention to a method of producing bisphenol A as disclosed in the patent literatures but by using a polycarbonate resin using, as a raw material, a bisphenol A confirmed to satisfy the criteria of the present invention after part of a lot of the bisphenol A (hereinafter sometimes abbreviated as "BPA") obtained as a raw material has been collected and analyzed for its concentrations of specific impurities, and a composition thereof.

Solution to Problem

The inventors of the present invention have found that a polycarbonate resin and a polycarbonate resin composition each having a satisfactory hue can be produced by using a bisphenol A satisfying the following: the amounts of isopropenylphenol (hereinafter sometimes abbreviated as "IPP") and a 2,4-isomer detected after the heating of the bisphenol A obtained as a raw material at 175° C. for 1 hour fall within specific ranges.

That is, the present invention includes the following.

1. A polycarbonate resin, including as a raw material, a bisphenol A having 100 ppm by mass or less of isopropenylphenol and 250 ppm by mass or less of 2-(2-hydroxyphenyl)-2-(4-hydroxyphenyl)propane, each detected after heating in air at 175° C. for 1 hour.

2. The polycarbonate resin according to Item 1, in which the bisphenol A serving as the raw material satisfies the following formula (i).

(Concentration of isopropenylphenol detected after heating at 175° C. for 1 hour)−(concentration of isopropenylphenol before heating at 175° C. for 1 hour)≤50 ppm by mass      Formula (i)

3. The polycarbonate resin according to Item 1 or 2, wherein the polycarbonate resin has a viscosity-average molecular weight of from 9,000 to 17,500.

4. A polycarbonate resin composition, comprising 100 parts by mass of (A) a polycarbonate resin containing 60 mass % or more of the polycarbonate resin of any one of Items 1 to 3, and 100 ppm by mass to 1,500 ppm by mass of (B) a phosphorus-based antioxidant.

5. The polycarbonate resin composition according to Item 4, wherein (B) the phosphorus-based antioxidant has a pentaerythritol structure.

6. The polycarbonate resin composition according to Item 4 or 5, wherein (B) the phosphorus-based antioxidant comprises bis(2,6-di-tert-butyl-4-methylphenyl)pentaerythritol diphosphite and/or bis(2,4-dicumylphenyl)pentaerythritol diphosphite.

7. The polycarbonate resin composition according to any one of Items 4 to 6, further comprising, with respect to 100 parts by mass of (A) the polycarbonate resin, 200 ppm by mass to 1,500 ppm by mass of (C) a polyorganosiloxane having a functional group.

8. The polycarbonate resin composition according to Item 7, wherein the functional group comprises at least one selected from the group consisting of an alkoxy group, an aryloxy group, a polyoxyalkylene group, a carboxyl group, a silanol group, an amino group, a mercapto group, an epoxy group, and a vinyl group.

9. The polycarbonate resin composition according to Item 7 or 8, wherein a difference between a refractive index of (C) the polyorganosiloxane and a refractive index of (A) the polycarbonate resin is 0.13 or less.

10. A molded body, which is obtained by molding the polycarbonate resin composition of any one of Items 4 to 9.

11. The molded body according to Item 10, wherein the molded body comprises a light-guiding plate.

12. A bisphenol A, having 100 ppm by mass or less of isopropenylphenol and 250 ppm by mass or less of 2-(2-hydroxyphenyl)-2-(4-hydroxyphenyl)propane, each detected after heating in air at 175° C. for 1 hour.

13. A method of producing a polycarbonate resin, including using as a raw material, a bisphenol A having 100 ppm by mass or less of isopropenylphenol and 250 ppm by mass or less of 2-(2-hydroxyphenyl)-2-(4-hydroxyphenyl)propane, each detected after heating in air at 175° C. for 1 hour.

Advantageous Effects of Invention

According to the present invention, there are provided a polycarbonate resin and a composition thereof that can provide a molded body having a satisfactory hue (low YI value).

DESCRIPTION OF EMBODIMENTS

<Polycarbonate Resin>
The present invention provides a polycarbonate resin, including as a raw material, a bisphenol A having 100 ppm by mass or less of isopropenylphenol and 250 ppm by mass or less of 2-(2-hydroxyphenyl)-2-(4-hydroxyphenyl)propane (hereinafter abbreviated as "2,4-isomer"), each detected after heating in air at 175° C. for 1 hour.

When the amount of isopropenylphenol is more than 100 ppm by mass, the hue of the polycarbonate resin using the bisphenol A as a raw material deteriorates. The amount of isopropenylphenol is preferably 50 ppm by mass or less. Isopropenylphenol is a compound represented by the following general formula (1).

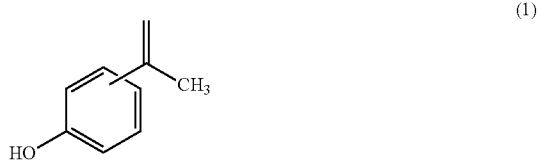

(1)

Isopropenylphenol is a substance incorporated as an impurity into the raw material bisphenol A together with, for example, the 2,4-isomer. Isopropenylphenol has been known as a decomposition product of bisphenol A, and has been known as a substance having high reactivity. It has been known that when bisphenol A is left to stand in air, bisphenol A changes into other impurities, such as a cyclic dimer in which two isopropenylphenol molecules are bonded to each other, and trisphenol produced by a reaction between bisphenol A and isopropenylphenol. The inventors of the present invention have found that even when the isopropenylphenol concentration itself of the raw material bisphenol A before the production of a polycarbonate is low, concern is raised in that an impurity produced by the change of isopropenylphenol in the bisphenol A is responsible for an influence on the hue of each of the polycarbonate resin and a resin composition using the resin.

In view of the foregoing, the inventors have paid attention to the fact that subjecting bisphenol A to a heating test increases its isopropenylphenol concentration, and hence have found that a polycarbonate resin and a resin composition each having a satisfactory hue can each be produced by using as a raw material, a bisphenol A having 100 ppm by mass or less of isopropenylphenol and 250 ppm by mass or less of 2-(2-hydroxyphenyl)-2-(4-hydroxyphenyl)propane, each detected after heating in air at 175° C. for 1 hour.

The 2,4-isomer is an impurity produced as a regioisomer at the time of the production of bisphenol A. When the amount of the 2,4-isomer is more than 250 ppm by mass, the hue of the bisphenol A deteriorates to cause a problem in terms of the quality of the resin. The amount of the 2,4-isomer is preferably 210 ppm by mass or less, more preferably 200 ppm by mass or less.

In addition, when the raw material bisphenol A has 50 ppm by mass or less of isopropenylphenol, and 210 ppm by mass or less or 200 ppm by mass or less of the 2,4-isomer, each detected after heating in air at 175° C. for 1 hour, a resin and a resin composition each having a more excellent hue can be obtained.

As described above, isopropenylphenol in the raw material bisphenol A has high reactivity and changes with time, and hence its concentration reduces with time. After having found that heating the raw material bisphenol A at 175° C. for 1 hour increases its isopropenylphenol concentration, the inventors of the present invention have considered that the phenomenon may be responsible for a variation in transparency of each of a polycarbonate resin and a resin composition obtained when the obtained bisphenol A is used as it is, and thus have reached the invention of the present application. When a difference between the isopropenylphenol concentrations before and after the heating test is small, a resin and a resin composition each having a more excellent hue can be obtained. In the present invention, it is desired that a difference between the concentration of isopropenylphenol detected after the heating of the raw material bisphenol A in air at 175° C. for 1 hour and the concentration thereof before the heating (initial value before the heating at 175° C. for 1 hour) be preferably 50 ppm by mass or less, more preferably 40 ppm by mass or less, still more preferably 35 ppm by mass or less. In one embodiment of the present invention, a bisphenol A satisfying the following formula (i) can be used as the raw material.

(Concentration of isopropenylphenol detected after heating at 175° C. for 1 hour)−(concentration of isopropenylphenol before heating at 175° C. for 1 hour)≤50 ppm by mass    Formula (i)

When the raw material bisphenol A in which the difference between the isopropenylphenol concentrations before and after the heating test is small is used as described above, in addition to a raw material in which the amount of isopropenylphenol detected after the heating test falls within the range of the present invention be used, a polycarbonate resin and a composition thereof each having a more excellent hue can be obtained.

Of course, when the raw material bisphenol A has 50 ppm by mass or less of isopropenylphenol, and 210 ppm by mass or less or 200 ppm by mass or less of the 2,4-isomer, each detected after heating in air at 175° C. for 1 hour, and the difference between the concentration of isopropenylphenol detected after the heating under the conditions and the concentration thereof before the heating (initial value before the heating at 175° C. for 1 hour) is preferably 50 ppm by mass or less, more preferably 40 ppm by mass or less, still more preferably 35 ppm by mass or less, a polycarbonate resin and a composition thereof each having a more excellent hue can be obtained.

The viscosity-average molecular weight of the polycarbonate resin of the present invention is preferably from 9,000 to 17,500, and more preferably from 11,000 to 15,500. The case where the viscosity-average molecular weight of the polycarbonate resin falls within the range is preferred because of the following reasons: a molding temperature suitable for the size of a molded article can be set, and hence the molded article suppresses yellow tint; and a molded body retaining a strength can be obtained.

The viscosity-average molecular weight is a value calculated from the equation $[\eta]=1.23\times10^{-5}\mathrm{MV}^{0.83}$ by using a limiting viscosity $[\eta]$ determined through the measurement of the viscosity of a methylene chloride solution at 20° C. with an Ubbelohde-type viscometer.

The content of methylene chloride in the polycarbonate resin of the present invention is preferably 200 ppm by mass or less, more preferably 50 ppm by mass or less, and still more preferably 20 ppm by mass or less. When the polycarbonate resin is produced by an interfacial condensation reaction method, methylene chloride having a low boiling point is used as an organic solvent. However, it has been known that unless the methylene chloride is sufficiently removed in a posttreatment, the methylene chloride remains as an impurity in the polycarbonate resin and hence the yellowing of the resin progresses. In addition, the corrosion of a die due to the chloride is liable to occur and the surface of the die is roughened. Accordingly, continuous use of the die may reduce the light-guiding property of the molded article.

The polycarbonate resin can be produced by causing the bisphenol A having 100 ppm by mass or less of isopropenylphenol and 250 ppm by mass or less of the 2,4-isomer, each detected after heating in air at 175° C. for 1 hour among the bisphenol A obtained as a raw material, to react with a carbonate precursor. The reaction is not particularly limited and a known method can be adopted therefor. The reaction is preferably performed by an interfacial polymerization method in the presence of an aqueous solution of an alkali compound and a water-insoluble organic solvent. The reaction can be performed in the presence of a polymerization catalyst as required.

Examples of the alkaline compound include: alkali metal hydroxides, such as sodium hydroxide and potassium hydroxide; and alkaline earth metal hydroxides, such as magnesium hydroxide and calcium hydroxide. Among them, an alkali metal hydroxide is preferred, and sodium hydroxide is more preferred. The dihydric phenol-based compound is preferably used as a mixture with the alkaline compound aqueous solution.

As the water-insoluble organic solvent, for example, a halogenatedhydrocarbon,such as methylene chloride, chlorobenzene, or chloroform, is preferred, and methylene chloride is more preferred.

Examples of the polymerization catalyst include tertiary amines and quaternary ammonium salts. Examples of the tertiaryamine include trimethylamine, triethylamine, and tripropylamine. Examples of the quaternary ammonium salt include trimethylbenzylammonium chloride and triethylammonium chloride. As the polymerization catalyst, a tertiary amine is preferred, and triethylamine is more preferred.

In addition, a molecular weight modifier may be used, as necessary. The molecular weight modifier is not particularly limited as long as the modifier is a monohydric phenol, and examples thereof include phenol, o-n-butylphenol, m-n-butylphenol, p-n-butylphenol, o-isobutylphenol, m-isobutylphenol, p-isobutylphenol, o-t-butylphenol, m-t-butylphenol, p-t-butylphenol, o-n-pentylphenol, m-n-pentylphenol, p-n-pentylphenol, o-n-hexylphenol, m-n-hexylphenol, p-n-hexylphenol, p-t-octylphenol, o-cyclohexylphenol, m-cyclohexylphenol, p-cyclohexylphenol, o-phenylphenol, m-phenylphenol, p-phenylphenol, o-n-nonylphenol, m-n-nonylphenol, p-n-nonylphenol, o-cumylphenol, m-cumylphenol, p-cumylphenol, o-naphthylphenol, m-naphthylphenol, p-naphthylphenol, 2,5-di-t-butylphenol,2,4-di-t-butylphenol, 3,5-di-t-butylphenol, 2,5-dicumylphenol, 3,5-dicumylphenol, p-cresol, a monoalkylphenol having a linear or branched alkyl group having 12 to 35 carbon atoms on average at the ortho-, meta-, or para-position, 3-pentadecylphenol, 9-(4-hydroxyphenyl)-9-(4-methoxyphenyl)fluorene, 9-(4-hydroxy-3-methylphenyl)-9-(4-methoxy-3-methylphenyl)fluor ene, and 4-(1-adamantyl)phenol. Among them, p-t-butylphenol, p-cumylphenol, and p-phenylphenol are preferred, and p-t-butylphenol is more preferred.

For example, the following phase-transfer catalyst may be preferably used as the catalyst: a tertiary amine or a salt thereof, a quaternary ammonium salt, or a quaternary phosphonium salt. Examples of the tertiary amine include triethylamine, tributylamine, N,N-dimethylcyclohexylamine, pyridine, and dimethylaniline. In addition, examples of the tertiary amine salt include hydrochlorides and bromates of those tertiary amines. Examples of the quaternary ammonium salt include trimethylbenzylammonium chloride, triethylbenzylammonium chloride, tributylbenzylammonium chloride, trioctylmethylammonium chloride, tetrabutylammonium chloride, and tetrabutylammonium bromide. Examples of the quaternary phosphonium salt include tetrabutylphosphonium chloride and tetrabutylphosphonium bromide. Each of those catalysts may be used alone, or two or more kinds thereof may be used in combination. Among the catalysts, tertiary amines are preferred, and triethylamine is particularly suitable. <Polycarbonate Resin Composition>
[(A) Polycarbonate Resin]

In another aspect of the present invention, there is provided a polycarbonate resin composition obtained by blending (A) a polycarbonate resin containing the polycarbonate resin of the present invention with (B) a phosphorus-based antioxidant to be described later.

The polycarbonate resin composition of the present invention may contain, as (A) the polycarbonate resin, a polycarbonate resin except the polycarbonate resin of the present invention to the extent that the resin does not affect the hue, transparency, mechanical characteristics, and the like of the composition. In that case, the ratio of the polycarbonate resin of the present invention in (A) the polycarbonate resin is preferably 60 mass % or more, more preferably 80 mass % or more, still more preferably 100 mass %. When two or more of polycarbonate resins are used as a mixture, the polycarbonate resins are desirably used after the viscosity-average molecular weight of the entirety of the polycarbonate resins has been adjusted to fall within the above-mentioned range. [(B) Phosphorus-Based Antioxidant]

In another aspect of the present invention, there can be provided a polycarbonate resin composition obtained by blending 100 parts by mass of (A) the polycarbonate resin with 100 ppm by mass to 1,500 ppm by mass, preferably 300 ppm by mass to 1,200 ppm by mass of (B) the phosphorus-based antioxidant. When the amount of the antioxidant is less than 100 ppm by mass, an effect as an antioxidant is not sufficient and hence an increase in YI value cannot be suppressed. Meanwhile, when the amount is more than 1,500 ppm by mass, the decomposition of the polycarbonate may progress owing to an acid generated by the decomposition of the antioxidant.

For example, the following antioxidant may be used as the phosphorus-based antioxidant: phosphorous acid, phosphonous acid, phosphonic acid, or esters thereof, or a tertiary phosphine. Among them, a phosphorous acid ester having a pentaerythritol structure represented by the following general formula (2) is preferred.

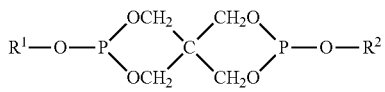
(2)

In the general formula (2), $R^1$ and $R^2$ each represent hydrogen, an alkyl group, a cycloalkyl group, or an aryl group. The cycloalkyl group and the aryl group may each be substituted by an alkyl group.

When $R^1$ and $R^2$ each represent an aryl group, $R^1$ and $R^2$ each preferably represent an aryl group represented by the following general formula (a), (b), or (c).

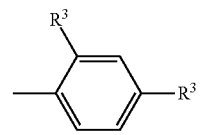
(a)

[In the formula (a), $R^3$ represents an alkyl group having 1 to 10 carbon atoms.]

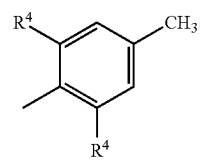
(b)

[In the formula (b), $R^4$ represents an alkyl group having 1 to 10 carbon atoms.]

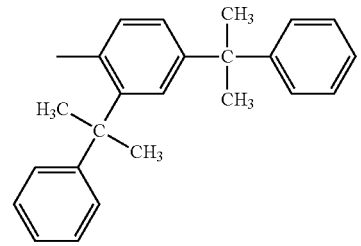
(c)

Specific examples thereof may include bis(2,6-di-tert-butyl-4-methylphenyl) pentaerythritol diphosphite represented by the following formula (3), bis(2,4-dicumylphenyl) pentaerythritol diphosphite represented by the following formula (4), and compounds represented by the following formulae (5) to (8).

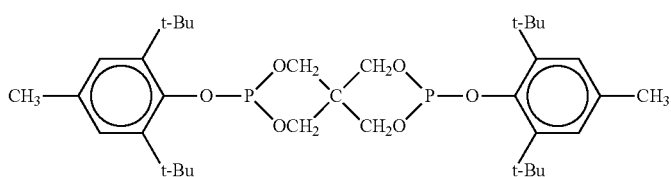
(3)

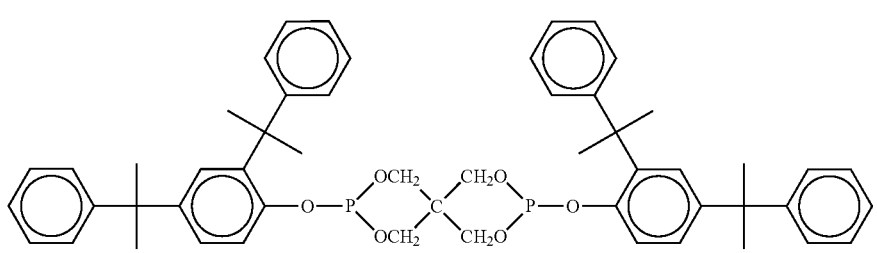
(4)

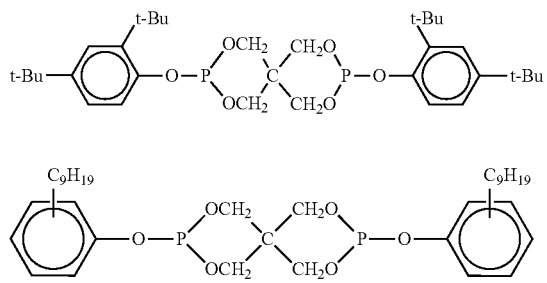

(5)

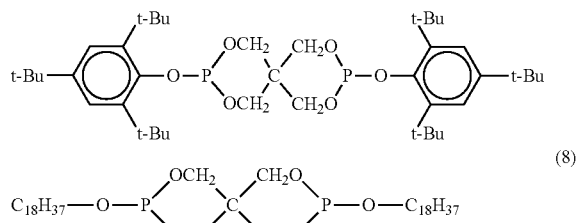

(6)

(7)

(8)

Bis(2,6-di-tert-butyl-4-methylphenyl)pentaerythritol diphosphite represented by the formula (3) [such as ADK STAB PEP-36: manufactured by ADEKA Corporation] and/or bis(2,4-dicumylphenyl)pentaerythritol diphosphite represented by the formula (4) [such as Doverphos S-9228PC: manufactured by Dover Chemical Corporation] is suitable in the present invention.

[(C) Polyorganosiloxane having Functional Group]

In addition, 200 ppm by mass to 1,500 ppm by mass, more preferably 300 ppm by mass to 1,200 ppm by mass of (C) a polyorganosiloxane having a functional group can be blended into the polycarbonate resin composition of the present invention, with respect to 100 parts by mass of (A) the polycarbonate resin. Together with any other component, blending (C) the polyorganosiloxane having a functional group at a content in the range of from 200 ppm by mass to 1,500 ppm by mass can improve the releasability of the molded article. Further, the blending can significantly reduce the occurrence of a silver streak and the amount of a die deposit even under a high-temperature molding condition largely exceeding 300° C., especially under a continuous molding condition.

The polyorganosiloxane having a functional group preferably has, as the functional group, at least one kind of functional group selected from the group consisting of an alkoxy group, an aryloxy group, a polyoxyalkylene group, a carboxyl group, a silanol group, an amino group, a mercapto group, an epoxy group, and a vinyl group.

The viscosity of the polyorganosiloxane having a functional group at 25° C. is preferably 10 mm$^2$/sec or more from the viewpoint of its lubricating effect, and is more preferably 200 mm$^2$/sec or less from the viewpoint of its dispersibility in the polycarbonate resin. From the foregoing viewpoints, the viscosity range of the polyorganosiloxane having a functional group is still more preferably from 20 mm$^2$/sec to 150 mm$^2$/sec, particularly preferably from 40 mm$^2$/sec to 120 mm$^2$/sec.

In order to prevent the transparency of the polycarbonate resin composition from reducing, a difference between the refractive index of the polyorganosiloxane having a functional group and the refractive index of the polycarbonate resin is preferably reduced to the extent possible, for example, to 0.13 or less. The refractive index of the polyorganosiloxane having a functional group is preferably 1.45 or more, more preferably 1.50 or more, still more preferably 1.52 or more because the refractive index of the polycarbonate resin is about 1.58.

[Additive]

Any other resin or an additive, such as an oxidation inhibitor, a weathering agent, a lubricant, a release agent, a plasticizer, a flowability improver, or a antistatic agent, can be added to the polycarbonate resin composition of the present invention at the time of its mixing or at the time of its molding to the extent that its physical properties are not impaired.

[Method of Producing Polycarbonate Resin Composition]

A method of producing the polycarbonate resin composition of the present invention is, for example, a method involving melting and kneading the respective components by a conventionally known method.

For example, the following method is appropriately selected: the respective components are dispersed and mixed with a high-speed mixer typified by a Tumbling mixer, a Henschel mixer, a ribbon blender, or a super mixer, and then the resultant is melted and kneaded with an extruder, a Banbury mixer, a roll, or the like.

The polycarbonate resin composition of the present invention can be suitably used in molding at high temperature exceeding 300° C. for producing a thin-walled molded article, and a molded article to be obtained has a low YI value. The polycarbonate resin composition of the present invention containing the polycarbonate resin using as a raw material, the bisphenol A having 100 ppm by mass or less of isopropenylphenol and 250 ppm by mass or less of 2-(2-hydroxyphenyl)-2-(4-hydroxyphenyl)propane, each detected after heating in air at 175° C. for 1 hour, can achieve a ΔYI representing a change in hue of a molded body of preferably 0.15 or less, more preferably 0.14 or less even when a molding time in, for example, high-temperature molding at 360° C. is extended from 30 seconds to 600 seconds. The foregoing means that even in long-term high-temperature molding, a molded article to be obtained is excellent in hue.

A molding method involving using the polycarbonate resin composition of the present invention is not particularly limited, and a molding method such as injection molding, injection compression molding, extrusion molding, or blow molding can be applied.

A molded article obtained by molding the polycarbonate resin composition of the present invention has a low YI value and is excellent in hue. Accordingly, the molded article can also be suitably used in a light-guiding member, such as a light-guiding plate having a long light-guiding length in which a required light transmission length is not the thickness direction of a thin-walled molded body but the longitudinal direction of a planar molded body. The molded body obtained by molding the polycarbonate resin composition of the present invention is preferably a light-guiding member, more preferably a light-guiding plate.

EXAMPLES

The present invention is described more specifically below byway of Examples. However, the present invention is by no means limited by these examples. Respective components, and measurement methods (calculation methods) for physical property values and the like used in Examples are as described below.
(B) Phosphorus-based Antioxidant
(B-1) ADK STAB PEP-36
[bis(2,6-di-tert-butyl-4-methylphenyl)pentaerythritol diphosphite, manufactured by ADEKA Corporation]
(B-2) Doverphos S-9228PC [bis(2,4-dicumylphenyl)pentaerythritol diphosphite, manufactured by Dover Chemical Corporation]
(C) Polyorganosiloxane having Functional Group KR-511 [manufactured by Shin-Etsu Chemical Co., Ltd., polyorganosiloxane having a methoxy group], refractive index: 1.52, viscosity: 25° C., 85.8 mm$^2$/sec
(1) Measurement of YI Value
A YI value was measured with a spectrophotometer "U-4100" (manufactured by Hitachi High-Technologies Corporation) under the conditions of illuminant C and 2-degree field of observer angle.
(2) Method of Measuring Viscosity-Average Molecular Weight
The limiting viscosity [η] of a methylene chloride solution at 20° C. was measured with an Ubbelohde-type viscosity tube, and a viscosity-average molecular weight was calculated from the following relational expression (Schnell's equation).

$$[\eta]=1.23\times10^{-5}\times Mv^{0.83}$$

Example 1

An obtained bisphenol A (initial IPP concentration: 5 ppm by mass, initial 2,4-isomer concentration: 102 ppm by mass) was heated under the following conditions. That is, 10 g of the bisphenol A was loaded into a colorimetric tube having a diameter of 30 mm to be used in the measurement of an APHA or the like, and was heated in an electric furnace at 175° C. After the heating for 1 hour, the colorimetric tube was removed from the electric furnace and cooled. After that, the solidified bisphenol A was removed and subjected to impurity analysis. The bisphenol A was analyzed for the concentration of isopropenylphenol (hereinafter sometimes abbreviated as "IPP") and the concentration of the 2,4-isomer by high performance liquid chromatography. A high performance liquid chromatograph (manufactured by Waters, model: 2695, column: manufactured by GL Sciences Inc., Inertsil (trademark) ODS-3V) was used in the analysis including the analysis of the initial concentration. The mobile phase which was 25 mass % aqueous solution of acetonitrile kept for 45 minutes, and then analysis mode changed to 3.5 mass %/min gradient mode. After having reached 100 mass % acetonitrile, this condition was retained for 5 minutes. The injection amount of the sample was set to 5.0 µL, a column temperature was set to 40° C., a flow rate was set to 1.0 mL/min, and an analysis wavelength was set to 277 nm.
As a result of the HPLC measurement, it is found that the IPP concentration was 37 ppm by mass and the 2,4-isomer concentration was 103 ppm by mass, each after the heating test. The results are shown in Table 1-1. A polycarbonate resin was produced by using a bisphenol A of the same lot as that of the bisphenol A as a raw material in accordance with the following production example.
Production Example: Production of Bisphenol A Polycarbonate Resin
(1) Polycarbonate Oligomer Synthesis Step
To 5.6 mass % aqueous sodium hydroxide, sodium dithionite was added in an amount of 2,000 ppm by mass relative to bisphenol A (hereinafter sometimes abbreviated as "BPA") to be dissolved later, and BPA obtained in this example was then dissolved therein so that the concentration of BPA became 13.5 mass %, to thereby prepare a solution of BPA in aqueous sodium hydroxide. The solution of BPA in aqueous sodium hydroxide, methylene chloride, and phosgene were continuously passed through a tubular reactor having an inner diameter of 6 mm and a tube length of 30 m at flow rates of 40 L/hr, 15 L/hr, and 4.0 kg/hr, respectively. The tubular reactor had a jacket portion, and cooling water was passed through the jacket to keep the reaction liquid at a temperature of 40° C. or less.
The reaction liquid that had exited the tubular reactor was continuously introduced into a baffled tank-type reactor having an internal volume of 40 L and provided with a sweptback blade, and then, 2.8 L/hr of the solution of BPA in aqueous sodium hydroxide, 0.07 L/hr of 25 mass % aqueous sodium hydroxide, 17 L/hr of water, and 0.64 L/hr of a 1 mass % triethylamine aqueous solution were further added to the reactor to perform a reaction.
The reaction liquid overflown from the tank-type reactor was continuously taken out and left to stand still to separate and remove an aqueous phase, and a methylene chloride phase was then collected. The concentration of the obtained polycarbonate oligomer was 325 g/L, and the concentration of a chloroformate group thereof was 0.77 mol/L.
(2) Polycarbonate Polymerization Step
After the temperature of the cooling solvent of a 50-liter tank-type reactor provided with a baffle board, a paddle-type stirring blade, and a cooling jacket had become 20° C. or less, 15 L of the oligomer solution, 8.9 L of methylene chloride, 192 g of p-tert-butylphenol, 0.7 mL of triethylamine, and a solution of BPA in aqueous sodium hydroxide (obtained by dissolving 1,185 g of BPA in an aqueous solution obtained by dissolving 647 g of NaOH and 2,000 ppm by mass of sodium dithionite with respect to BPA to be dissolved later in 9.5 L of water) were added to perform a polymerization reaction for 30 minutes. After that, 0.8 mL of triethylamine was added to the resultant and the mixture was further stirred for 30 minutes.
15 Liters of methylene chloride was added to the mixture for dilution, and then the diluted mixture was separated into an organic phase containing a polycarbonate resin, and an aqueous phase containing excess BPA and NaOH, followed by the isolation of the organic phase. The resultant solution of the polycarbonate resin in methylene chloride was sequentially washed with 15 vol % each of 0.03 mol/L aqueous NaOH and 0.2 mol/L hydrochloric acid with respect to the solution. Next, washing with pure water was repeated until an electric conductivity in the aqueous phase after the washing became 0.05 µS/m or less. A solution of the polycarbonate resin in dichloromethane obtained by the washing was concentrated and pulverized, and the resultant flake was dried under reduced pressure at 100° C. to provide (A) a polycarbonate resin flake. The viscosity-average molecular weight of the flake is shown in Table 1. The refractive index of the polycarbonate resin obtained in each of Example 1 and Examples 2 to 6 to be described later was 1.58.
100 Parts by mass of (A) the polycarbonate resin flake thus obtained was dry-blended with 600 ppm by mass of (B-1) the phosphorus-based antioxidant and 500 ppm by mass of (C) the polyorganosiloxane having a functional group, and then the blend was melted and kneaded with a single screw extruder at a cylinder temperature of 260° C. The resultant strand was passed through a water tank to be cooled, and was then pelletized to prepare a polycarbonate resin composition. The resin pellet was dried at 110° C. for 5 hours, and then a flat plate-shaped molded body measuring 25 mm by 35 mm by 3.0 mm thick was produced from the pellet with an injection molding machine "Toshiba EC40N" (manufactured by Toshiba Machine Co., Ltd., clamping force: 40 tons) under each of the following conditions: (i) a cylinder temperature setting of 360° C., a die temperature of 80° C., and a cycle time of 30 seconds; and (ii) a cylinder temperature setting of 360° C., a die temperature of 80° C., and a cycle time of 600 seconds.

The YI values of the molded bodies obtained under the respective molding conditions (i) and (ii) were measured. The results are shown in Table 2-1.

Example 2

A bisphenol A having an initial IPP concentration of 6 ppm by mass and an initial 2,4-isomer concentration of 204 ppm by mass was subjected to a heating test in the same manner as in Example 1. Its IPP concentration and 2,4-isomer concentration after the heating test were 32 ppm by mass and 206 ppm by mass, respectively. The results are shown in Table 1-1.

100 Parts by mass of (A) a polycarbonate resin produced by using a bisphenol A of the same lot as that of the bisphenol A as a raw material in the same manner as in Example 1 was dry-blended with (B-1) the phosphorus-based antioxidant and (C) the polyorganosiloxane having a functional group at ratios shown in Table 2-1, and then a polycarbonate resin composition was prepared in the same manner as in Example 1. Molded bodies were produced from the composition, and their YI values were measured. The results are shown in Table 2-1.

Example 3

A bisphenol A having an initial IPP concentration of 4 ppm by mass and an initial 2,4-isomer concentration of 56 ppm by mass was subjected to a heating test in the same manner as in Example 1. Its IPP concentration and 2,4-isomer concentration after the heating test were 39 ppm by mass and 56 ppm by mass, respectively. The results are shown in Table 1-1.

100 Parts by mass of (A) a polycarbonate resin produced by using a bisphenol A of the same lot as that of the bisphenol A as a raw material in the same manner as in Example 1 was dry-blended with (B-1) the phosphorus-based antioxidant and (C) the polyorganosiloxane having a functional group at ratios shown in Table 2-1, and then a polycarbonate resin composition was prepared in the same manner as in Example 1. Molded bodies were produced from the composition, and their YI values were measured. The results are shown in Table 2-1.

Example 4

A bisphenol A having an initial IPP concentration of 12 ppm by mass and an initial 2,4-isomer concentration of 103 ppm by mass was subjected to a heating test in the same manner as in Example 1. Its IPP concentration and 2,4-isomer concentration after the heating test were 39 ppm by mass and 103 ppm by mass, respectively. The results are shown in Table 1-1.

100 Parts by mass of (A) a polycarbonate resin produced by using a bisphenol A of the same lot as that of the bisphenol A as a raw material in the same manner as in Example 1 was dry-blended with (B-2) the phosphorus-based antioxidant and (C) the polyorganosiloxane having a functional group at ratios shown in Table 2-1, and then a polycarbonate resin composition was prepared in the same manner as in Example 1. Molded bodies were produced from the composition, and their YI values were measured. The results are shown in Table 2-1.

Example 5

A bisphenol A having an initial IPP concentration of 6 ppm by mass and an initial 2,4-isomer concentration of 142 ppm by mass was subjected to a heating test in the same manner as in Example 1. Its IPP concentration and 2,4-isomer concentration after the heating test were 35 ppm by mass and 147 ppm by mass, respectively. The results are shown in Table 1-1.

100 Parts by mass of (A) a polycarbonate resin produced by using a bisphenol A of the same lot as that of the bisphenol A as a raw material in the same manner as in Example 1 was dry-blended with (B-2) the phosphorus-based antioxidant and (C) the polyorganosiloxane having a functional group at ratios shown in Table 2-1, and then a polycarbonate resin composition was prepared in the same manner as in Example 1. Molded bodies were produced from the composition, and their YI values were measured. The results are shown in Table 2-1.

Example 6

A bisphenol A having an initial IPP concentration of 19 ppm by mass and an initial 2,4-isomer concentration of 208 ppm by mass was subjected to a heating test in the same manner as in Example 1. Its IPP concentration and 2,4-isomer concentration after the heating test were 68 ppm by mass and 211 ppm by mass, respectively. The results are shown in Table 1-1.

100 Parts by mass of (A) a polycarbonate resin produced by using a bisphenol A of the same lot as that of the bisphenol A as a raw material in the same manner as in Example 1 except that the amount of p-tert-butylphenol was changed to 147 g was dry-blended with (B-2) the phosphorus-based antioxidant and (C) the polyorganosiloxane having a functional group at ratios shown in Table 2-1, and then a polycarbonate resin composition was prepared in the same manner as in Example 1. Molded bodies were produced from the composition, and their YI values were measured. The results are shown in Table 2-1.

Comparative Example 1

A bisphenol A having an initial IPP concentration of 28 ppm by mass and an initial 2,4-isomer concentration of 285 ppm by mass was subjected to a heating test in the same manner as in Example 1. Its IPP concentration and 2,4-isomer concentration after the heating test were 30 ppm by mass and 289 ppm by mass, respectively. The results are shown in Table 1-2.

100 Parts by mass of (A) a polycarbonate resin produced by using a bisphenol A of the same lot as that of the bisphenol A as a raw material in the same manner as in Example 1 was dry-blended with (B-1) the phosphorus-based antioxidant and (C) the polyorganosiloxane having a functional group at ratios shown in Table 2-2, and then a polycarbonate resin composition was prepared in the same manner as in Example 1. Molded bodies were produced from the composition, and their YI values were measured. The results are shown in Table 2-2.

Comparative Example 2

A bisphenol A having an initial IPP concentration of 245 ppm by mass and an initial 2,4-isomer concentration of 142 ppm by mass was subjected to a heating test in the same manner as in Example 1. Its IPP concentration and 2,4-isomer concentration after the heating test were 327 ppm by mass and 143 ppm by mass, respectively. The results are shown in Table 1-2.

100 Parts by mass of (A) a polycarbonate resin produced by using a bisphenol A of the same lot as that of the bisphenol A as a raw material in the same manner as in Example 1 was dry-blended with (B-1) the phosphorus-based antioxidant and (C) the polyorganosiloxane having a functional group at ratios shown in Table 2-2, and then a polycarbonate resin composition was prepared in the same manner as in Example 1. Molded bodies were produced from the composition, and their YI values were measured. The results are shown in Table 2-2.

TABLE 1-1

Results of heating test of raw material bisphenol A

|  |  |  | Example 1 | Example 2 | Example 3 | Example 4 | Example 5 | Example 6 |
|---|---|---|---|---|---|---|---|---|
| IPP | ppm by mass | Initial | 5 | 6 | 4 | 12 | 6 | 19 |
|  |  | 1 Hour after heating | 37 | 32 | 39 | 39 | 35 | 68 |
| 2,4-Isomer | ppm by mass | Initial | 102 | 204 | 56 | 103 | 142 | 208 |
|  |  | 1 Hour after heating | 103 | 206 | 56 | 103 | 147 | 211 |

TABLE 1-2

Results of heating test of raw material bisphenol A

|  |  |  | Comparative Example 1 | Comparative Example 2 |
|---|---|---|---|---|
| IPP | ppm by mass | Initial | 28 | 245 |
|  |  | 1 Hour after heating | 30 | 327 |
| 2,4-Isomer | ppm by mass | Initial | 285 | 142 |
|  |  | 1 Hour after heating | 289 | 143 |

TABLE 2-1

|  |  | Example 1 | Example 2 | Example 3 | Example 4 | Example 5 | Example 6 |
|---|---|---|---|---|---|---|---|
| (A) PC resin | parts by mass | 100 | 100 | 100 | 100 | 100 | 100 |
| (B-1) Phosphorus-based antioxidant | ppm by mass | 600 | 1,200 | 300 |  |  |  |
| (B-2) Phosphorus-based antioxidant | ppm by mass |  |  |  | 600 | 600 | 1,000 |
| (C) Polyorganosiloxane | ppm by mass | 500 | 1,000 | 500 | 300 | 500 | 500 |
| Viscosity-average molecular weight | ppm by mass | 14,800 | 14,700 | 15,200 | 14,900 | 15,100 | 16,800 |
| Molded body YI (measuring 25 mm by 35 mm by 3.0 mm thick) | 30 seconds @ 360° C. | 1.11 | 1.17 | 1.20 | 1.18 | 1.15 | 1.18 |
| Molded body YI (measuring 25 mm by 35 mm by 3.0 mm thick) | 600 seconds @ 360° C. | 1.25 | 1.20 | 1.31 | 1.27 | 1.23 | 1.33 |
| ΔYI |  | 0.14 | 0.03 | 0.11 | 0.09 | 0.08 | 0.15 |

TABLE 2-2

|  |  | Comparative Example 1 | Comparative Example 2 |
|---|---|---|---|
| (A) PC resin | parts by mass | 100 | 100 |
| (B-1) Phosphorus-based antioxidant | ppm by mass | 600 | 600 |
| (B-2) Phosphorus-based antioxidant | ppm by mass |  |  |
| (C) Polyorganosiloxane | ppm by mass | 500 | 500 |
| Viscosity-average molecular weight | ppm by mass | 14,900 | 14,900 |
| Molded body YI (measuring 25 mm by 35 mm by 3.0 mm thick) | 30 seconds @ 360° C. | 1.31 | 1.32 |
| Molded body YI (measuring 25 mm by 35 mm by 3.0 mm thick) | 600 seconds @ 360° C. | 1.48 | 1.61 |
| ΔYI |  | 0.17 | 0.29 |

Comparison between Examples 1 to 6, and Comparative Examples 1 and 2 of Tables 1-1 and 1-2 shows the following.

It is found that the ΔYI value of the molded body of the polycarbonate resin composition produced by using the bisphenol A of the present invention having 100 ppm by mass or less of isopropenylphenol and 250 ppm by mass or less of the 2,4-isomer, each detected after heating in air at 175° C. for 1 hour, is 0.15 or less, and hence the molded body maintains a satisfactory hue even when a molding time lengthens. Meanwhile, it is found from their YI values that the molded bodies of the polycarbonate resin compositions produced by using the bisphenol A of Comparative Example 1 in which the amount of the 2,4-isomer detected after the heating test at 175° C. for 1 hour is more than 250 ppm by mass and the bisphenol A of Comparative Example 2 in which the amount of isopropenylphenol is more than 100 ppm by mass cannot each obtain a satisfactory hue.

INDUSTRIAL APPLICABILITY

According to the present invention, there are provided a polycarbonate resin and a polycarbonate resin composition that can provide a molded body having a satisfactory hue (low YI value). The polycarbonate resin composition can be suitably used as a light-guiding member.

The invention claimed is:

1. A process for producing a polycarbonate resin, comprising: screening a bisphenol A having 100 ppm by mass or less of isopropenylphenol concentration and 250 ppm by mass or less of 2-(2-hydroxyphenyl)-2-(4-hydroxyphenyl) propane concentration, each detected after heating in air at 175° C. for 1 hour, and producing a polycarbonate resin by subjecting the screened bisphenol A and a carbonate precursor to a reaction by an interfacial polymerization method in the presence of an aqueous solution of an alkali compound and a water-insoluble organic solvent.

2. The process for producing a polycarbonate resin according to claim 1, wherein the bisphenol A serving as the raw material satisfies the following formula (i)

(Concentration of isopropenylphenol detected after heating at 175° C. for 1 hour)−(concentration of isopropenylphenol before heating at 175° C. for 1 hour)≤50 ppm by mass     Formula (i).

3. The process for producing a polycarbonate resin according to claim 1, wherein the polycarbonate resin has a viscosity-average molecular weight of from 9,000 to 17,500.

4. The process for producing a polycarbonate resin according to claim 1, wherein the isopropenylphenol concentration is 50 ppm by mass or less.

5. The process for producing a polycarbonate resin according to claim 1, wherein the 2-(2-hydroxyphenyl)-2-(4-hydroxyphenyl)propane concentration is 210 ppm by mass or less.

6. The process for producing a polycarbonate resin according to claim 1, wherein a difference between the concentration of isopropenylphenol detected after the heating of bisphenol A in air at 175° C. for 1 hour and the concentration thereof before the heating (initial value before the heating at 175° C. for 1 hour) is 40 ppm by mass or less.

7. The process for producing a polycarbonate resin according to claim 1, wherein the water-insoluble organic solvent comprises methylene chloride.

8. The process for producing a polycarbonate resin according to claim 1, wherein the content of methylene chloride in the polycarbonate resin is 200 ppm by mass or less.

9. A process for producing a polycarbonate resin composition, comprising producing a polycarbonate resin according to the process of claim 1, and blending 100 parts by mass of (A) a polycarbonate resin containing 60 mass % or more of the obtained polycarbonate resin, and 100 ppm by mass to 1,500 ppm by mass of (B) a phosphorus-based antioxidant.

10. The process for producing a polycarbonate resin composition according to claim 9, wherein (B) the phosphorus-based antioxidant has a pentaerythritol structure.

11. The process for producing a polycarbonate resin composition according to claim 9, wherein (B) the phosphorus-based antioxidant comprises bis(2,6-di-tert-butyl-4-methylphenyl)pentaerythritol diphosphite and/or bis(2,4-dicumylphenyl)pentaerythritol diphosphite.

12. The process for producing a polycarbonate resin composition according to claim 9, wherein a ratio of the polycarbonate resin that is obtained by the process for producing a polycarbonate resin according to claim 1 is 80 mass % or more.

13. The process for producing a polycarbonate resin composition according to claim 9, wherein comprising a step of blending 300 ppm by mass to 1,200 ppm by mass of (B) the phosphorus-based antioxidant based on 100 parts by mass of (A) the polycarbonate resin.

14. The process for producing a polycarbonate resin composition according to claim 9, further comprising blending, with respect to 100 parts by mass of (A) the polycarbonate resin, 200 ppm by mass to 1,500 ppm by mass of (C) a polyorganosiloxane having a functional group.

15. The process for producing a polycarbonate resin composition according to claim 14, wherein the functional group comprises at least one selected from the group consisting of an alkoxy group, an aryloxy group, a polyoxyalkylene group, a carboxyl group, a silanol group, an amino group, a mercapto group, an epoxy group, and a vinyl group.

16. The process for producing a polycarbonate resin composition according to claim 14, wherein a difference between a refractive index of (C) the polyorganosiloxane and a refractive index of (A) the polycarbonate resin is 0.13 or less.

17. The process for producing a polycarbonate resin composition according to claim 14, wherein the viscosity of (C) the polyorganosiloxane at 25° C. is 10 mm$^2$/sec or more and 200 mm$^2$/sec or less.

18. A process for producing a molded body, comprising: producing a polycarbonate resin composition by the process of claim 9, and molding the polycarbonate resin composition.

19. The molded body according to claim 18, wherein the molded body comprises a light-guiding plate.

20. The process for producing a molded body according to claim 18, wherein the molded body is a light-guiding member.

* * * * *